(12) United States Patent
Park

(10) Patent No.: US 10,806,752 B2
(45) Date of Patent: Oct. 20, 2020

(54) PHARMACEUTICAL COMPOSITION CONTAINING SULGLYCOTIDE OR PHARMACEUTICALLY ACCEPTABLE SALT THEREOF FOR PREVENTING OR TREATING DRY EYE

(71) Applicant: IMDPHARM INC., Daejeon (KR)

(72) Inventor: Young-Joon Park, Seoul (KR)

(73) Assignee: IMDPHARM INC., Daejeon (KR)

( * ) Notice: Subject to any disclaimer, the term of this patent is extended or adjusted under 35 U.S.C. 154(b) by 0 days.

(21) Appl. No.: 16/477,711

(22) PCT Filed: Jan. 4, 2018

(86) PCT No.: PCT/KR2018/000149
§ 371 (c)(1),
(2) Date: Jul. 12, 2019

(87) PCT Pub. No.: WO2018/131835
PCT Pub. Date: Jul. 19, 2018

(65) Prior Publication Data
US 2019/0358255 A1 Nov. 28, 2019

(30) Foreign Application Priority Data
Jan. 13, 2017 (KR) .......................... 10-2017-0006118

(51) Int. Cl.
| | | |
|---|---|---|
| *A61K 9/00* | (2006.01) | |
| *A61K 9/08* | (2006.01) | |
| *A61K 38/17* | (2006.01) | |
| *A61K 31/726* | (2006.01) | |

(52) U.S. Cl.
CPC .......... *A61K 31/726* (2013.01); *A61K 9/0048* (2013.01); *A61K 9/08* (2013.01); *A61K 38/1709* (2013.01)

(58) Field of Classification Search
None
See application file for complete search history.

(56) References Cited

U.S. PATENT DOCUMENTS

| | | | |
|---|---|---|---|
| 4,818,537 A | 4/1989 | Guo | |
| 5,800,807 A | 9/1998 | Hu et al. | |
| 6,384,081 B2 | 5/2002 | Berman | |
| 7,029,712 B1* | 4/2006 | Thornton | ............... A61K 31/07 |
| | | | 424/523 |
| 7,662,777 B2 | 2/2010 | Iacobelli et al. | |
| 2002/0013345 A1 | 1/2002 | Berman | |
| 2008/0050335 A1 | 2/2008 | Faour et al. | |
| 2008/0234180 A1 | 9/2008 | Iacobelli et al. | |
| 2016/0000809 A1* | 1/2016 | Lee | ..................... A61K 31/425 |
| | | | 514/20.8 |

FOREIGN PATENT DOCUMENTS

| | | |
|---|---|---|
| KR | 10-2007-0031933 A | 3/2007 |
| KR | 10-2009-0053892 A | 5/2009 |
| KR | 10-2012-0020534 A | 3/2012 |
| KR | 10-2012-0094253 A | 8/2012 |

OTHER PUBLICATIONS

Chen et al., "Altered Morphology and Function of the Lacrimal Functional Unit in Protein Kinase Calpha Knockout Mice", Invest Ophthalmol Vis Sci., 2010, vol. 51, No. 11, pp. 5592-5600.
De Paiva et al., "Apical Corneal Barrier Disruption in Experimental Murine Dry Eye Is Abrogated by Methylprednisolone and Doxycycline", Invest Ophthalmol Vis Sci., 2006, vol. 47, No. 7, pp. 2847-2856.
Rashid et al., "Topical Omega-3 and Omega-6 Fatty Acids for Treatment of Dry Eye", Arch Ophthalmol., 2008, vol. 126, No. 2, pp. 219-225.

* cited by examiner

*Primary Examiner* — Leigh C Maier
(74) *Attorney, Agent, or Firm* — Vorys, Sater, Seymour & Pease LLP; Mih Suhn Koh

(57) ABSTRACT

Provided is a method of preventing and treating a dry eye syndrome comprising administering a pharmaceutical composition comprising sulglycotide or its pharmaceutically acceptable salt as an active ingredient.

7 Claims, 6 Drawing Sheets

PHARMACEUTICAL COMPOSITION CONTAINING SULGLYCOTIDE OR PHARMACEUTICALLY ACCEPTABLE SALT THEREOF FOR PREVENTING OR TREATING DRY EYE

TECHNICAL FIELD

The present invention relates to a pharmaceutical composition for preventing or treating dry eye syndrome comprising sulglycotide or its pharmaceutically acceptable salt.

BACKGROUND ART

Dry eye syndrome is an ophthalmic disease referred to as keratoconjunctivitis sicca, occurring worldwide in 5.5 to 15% of adults. Dry eye syndrome, which is is considered as a multifunctional disorder in the tear film and the ocular surface, causes discomfort, visual impairment, and even eye surface damages due to tear film instability. The main physiological function of the tear film is lubrication of the ocular surface and inner eyelid. The tear film also provides nutrients to the eye surface, provides a smooth, even optical surface to the eye, and protects the eye surface. The tear film consists of mucus components, aqueous components, and lipids. A problem in lacrimal secretion leads to cause dry eye syndrome. Dry eye syndrome causes not only lack of tears but also ocular inconveniences and instabilities of the tear layer due to inflammation in the tears and eye surface (cornea and conjunctiva), thereby causing damages to the ocular surface, which results in ocular pain, irregular corneal surface, corneal ulcer, and decreased vision. Changed corneal permeability in chronic dry eye syndrome causes inflammation and increases the cytokines that mediate inflammation in tears. Depending on the severity of the disease, the patient often develops a reversible squameous metaphase and punctate erosions in the ocular epithelium. Secondary diseases that can be triggered by dry eye syndrome include fungal keratitis, microbial keratitis, corneal angiogenesis, and ocular surface keratinization.

Several approaches to the treatment of dry eye syndrome have been attempted. A common approach is to supplement and stabilize the tear layer in the eye with a buffered isotonic saline solution or artificial tears containing a water-soluble polymer. The artificial tears contain e.g., carboxymethyl cellulose and its sodium salt (CMC, carmellose), polyvinyl alcohol, hydroxypropyl methylcellulose (HPMC, hypromellose), hyaluronic acid or its sodium salt, hydroxypropyl guar gum, and so on. Another approach includes providing a lubricating material instead of artificial tears. For example, U.S. Pat. No. 4,818,537 discloses the use of a lubricating liposome composition, and U.S. Pat. No. 5,800,807 discloses a composition for treating dry eye syndrome comprising glycerin and propylene glycol.

DISCLOSURE

Technical Problem

The present inventor carried out various researches in order to develop a therapeutic agent capable of preventing or treating dry eye syndrome effectively. Surprisingly, it has been found by the present invention that the administration of sulglycotide (which is conventionally used as a therapeutic agent for peptic ulcer, gastro-esophageal reflux disease, and so on) to a dry eye animal model increases tear production remarkably, improves corneal surface irregularities, increases conjunctival goblet cell densities, and decreases the inflammatory cytokines in the ocular surface and the lacrimal gland; and therefore that sulglycotide can be usefully applied for treating dry eye syndrome.

Therefore, it is an object of the present invention to provide a pharmaceutical composition for preventing or treating dry eye syndrome comprising sulglycotide or its pharmaceutically acceptable salt as an active ingredient.

Technical Solution

In accordance with an aspect of the present invention, there is provided a pharmaceutical composition for preventing or treating dry eye syndrome comprising sulglycotide or its pharmaceutically acceptable salt as an active ingredient.

In the pharmaceutical composition of the present invention, sulglycotide or its pharmaceutically acceptable salt may be present in a concentration ranging from 0.01 w/v % to 30 w/v %. The pharmaceutical composition may have the dosage form of an eye drop formulation. The eye drop formulation may be in the form of an aqueous solution or an aqueous suspension.

The pharmaceutical composition of the present invention may comprise one or more carriers or excipients selected from the group consisting of a buffering agent, a viscosity-adjusting agent, an isotonic agent, an antioxidant, a chelating agent, and a pH-adjusting agent, in addition to sulglycotide or its pharmaceutically acceptable salt, in an aqueous medium.

In an embodiment, the viscosity-adjusting agent may be one or more selected from the group consisting of polyvinyl alcohol, polyvinylpyrrolidone, methyl cellulose, hydroxypropyl methylcellulose, hydroxyethyl cellulose, carboxymethyl cellulose, and hydroxypropyl cellulose, preferably may be polyvinylpyrrolidone or hydroxypropyl methylcellulose.

Advantageous Effects

It has been found by the present invention that the administration of sulglycotide to a dry eye animal model increases tear production remarkably, improves corneal surface irregularities, increases conjunctival goblet cell densities, and decreases the inflammatory cytokines in the eye surface and the lacrimal gland. Therefore, the pharmaceutical composition according to the present invention can be usefully applied for preventing or treating dry eye syndrome.

BEST MODE

Figure 1:
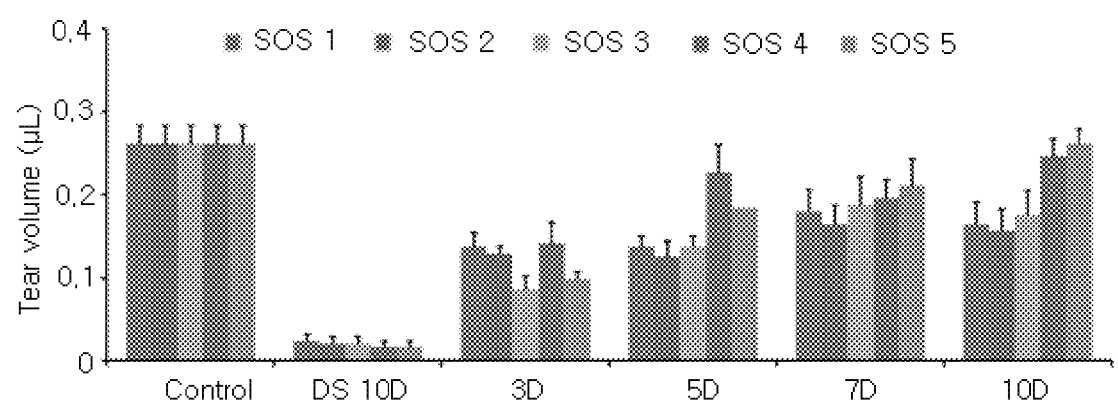
FIG. 1 shows the effects of the sulglycotide-containing eye drop solutions on tear production in the dry eye animal models (DED).

The present invention provides a pharmaceutical composition for preventing or treating dry eye syndrome comprising sulglycotide or its pharmaceutically acceptable salt as an active ingredient.

Sulglycotide is a material known as a sulfuric polyester of a glycopeptide obtained by extraction from the mucosal membrane of pig stomach or duodenum. Sulglycotide, which is used as a gastro-protective agent and an antiulcer agent, is not absorbed in the gastro-intestinal tract and is known to produce its effects only within the gastric lumen. Sulglycotide is generally administered as a gastro-protective agent to the subjects whose stomach walls are attacked by drugs such as aspirin and taurocholic acid, or non-steroidal anti-inflammatory drugs (NSAID). It has been newly found by the present invention that the administration of sulglycotide to a dry eye animal model increases tear production remarkably, improves corneal surface irregularities, increases conjunctival goblet cell densities, and decreases the inflammatory cytokines in the eye surface and the lacrimal gland.

In the pharmaceutical composition of the present invention, sulglycotide may be used in a non-salt form. And also, said sulglycotide may be used in the form of a pharmaceutically acceptable salt thereof, which may be prepared appropriately by a person having ordinary skill in the art.

In the pharmaceutical composition of the present invention, the dosage of sulglycotide or its pharmaceutically acceptable salt may be changed according to the patient's age, body weight, sex, dosage form, health condition and severity of diseases. For example, the dosage may range from 0.1 to 300 mg/day, preferably from 0.5 to 100 mg/day, more preferably from 1 to 60 mg/day, based on adult patients having 70 kg body weight. The administration may be carried out in an appropriate interval, e.g., in a single dose or in divided doses per day, according to the doctor's or pharmacist's instruction. In an embodiment, sulglycotide or its pharmaceutically acceptable salt may be present in a concentration ranging from 0.01 w/v % to 30 w/v %, preferably from 0.1 w/v % to 10 w/v %, but not limited thereto.

Preferably, the pharmaceutical composition may have the dosage form of an eye drop formulation. The eye drop formulation may be in the form of an aqueous solution or an aqueous suspension.

The pharmaceutical composition of the present invention may further comprise a carrier or excipient conventionally used in the field of an eye drop formulation. For example, the pharmaceutical composition of the present invention may comprise one or more carriers or excipients selected from the group consisting of a buffering agent, a viscosity-adjusting agent, an isotonic agent, an antioxidant, a chelating agent, and a pH-adjusting agent, in addition to sulglycotide or its pharmaceutically acceptable salt, in an aqueous medium.

Examples of the buffering agent include the buffering agents conventionally used in the field of an eye drop formulation, e.g., phosphoric acid or a salt thereof, boric acid or a salt thereof, carbonic acid or a salt thereof, citric acid or a salt thereof, acetic acid or a salt thereof, maleic acid or a salt thereof, succinic acid or a salt thereof, tartaric acid or a salt thereof, and so on. And also, the buffering agent may be in the form of a buffer solution such as a phosphoric acid/phosphate buffer (phosphate buffer solution), a boric acid/borate buffer (borate buffer solution), and so on.

Examples of the viscosity-adjusting agent may be one or more selected from the group consisting of polyvinyl alcohol, polyvinylpyrrolidone, methyl cellulose, hydroxypropyl methylcellulose, hydroxyethyl cellulose, carboxymethyl cellulose, and hydroxypropyl cellulose. The viscosity-adjusting agent may be preferably polyvinylpyrrolidone or hydroxypropyl methylcellulose, more preferably hydroxypropyl methylcellulose.

Examples of the isotonic agent include sodium chloride, potassium chloride, calcium chloride, sorbitol, mannitol, and so on.

Examples of the antioxidant include ascorbic acid or its ester, sodium bisulphite, butylated hydroxytoluene, butylated hydroxyanisole, tocopherol, and so on.

Examples of the chelating agent include ethylenediaminetetraacetic acid (EDTA), ethylenediamine, and so on.

Examples of the pH-adjusting agent include hydrochloric acid, amino acid, alkali metal hydroxide, alkali earth metal hydroxide, and so on.

The pharmaceutical composition of the present invention may comprise a hydrating agent, a sweetening agent, a flavoring agent, an emulsifier, a suspending agent, a preservative, and so on conventionally used in the field of an eye drop formulation, in addition to said carriers or excipients. The pharmaceutical composition of the present invention in the form of an eye drop formulation may be prepared e.g., by dissolving sulglycotide or its pharmaceutically acceptable salt in an aqueous medium (for example, water or a buffer solution) under stirring and dissolving or suspending said carriers or excipients additionally. Typically, the resulting solution or suspension is subject to sterile filtration to give an eye drop formulation form.

The present invention will be described in further detail with reference to the following examples and experimental examples. These examples and experimental examples are for illustrative purposes only and are not intended to limit the scope of the present invention.

Example 1

After phosphoric acid (0.0425 g), sodium hydrogen phosphate (4.43 g), and potassium dihydrogen phosphate (0.29 g) were dissolved in purified water (400 mL) under stirring at 50 rpm, sulglycotide (5 g) was dissolved therein. Sodium chloride (2.6 g) was dissolved in the resulting solution. Purified water was added to the resulting solution so as to adjust the final volume thereof to 500 ml. The resulting solution was subject to sterile filtration with a 0.22 µm PVDF syringe filter to prepare a 1 w/v % eye drop solution.

Example 2

After phosphoric acid (0.0425 g), sodium hydrogen phosphate (4.43 g), and potassium dihydrogen phosphate (0.29 g) were dissolved in purified water (400 mL) under stirring at 50 rpm, sulglycotide (10 g) was dissolved therein. Sodium chloride (2.4 g) was dissolved in the resulting solution. Purified water was added to the resulting solution so as to adjust the final volume thereof to 500 ml. The resulting solution was subject to sterile filtration with a 0.22 µm PVDF syringe filter to prepare a 2 w/v % eye drop solution.

Example 3

After phosphoric acid (0.0425 g), sodium hydrogen phosphate (4.43 g), and potassium dihydrogen phosphate (0.29 g)

were dissolved in purified water (400 mL) under stirring at 50 rpm, sulglycotide (15 g) was dissolved therein. Sodium chloride (2.2 g) was dissolved in the resulting solution. Purified water was added to the resulting solution so as to adjust the final volume thereof to 500 ml. The resulting solution was subject to sterile filtration with a 0.22 μm PVDF syringe filter to prepare a 3 w/v % eye drop solution.

Example 4

After phosphoric acid (0.0425 g), sodium hydrogen phosphate (4.43 g), and potassium dihydrogen phosphate (0.29 g) were dissolved in purified water (400 mL) under stirring at 50 rpm, sulglycotide (20 g) was dissolved therein. Sodium chloride (2.0 g) was dissolved in the resulting solution. Purified water was added to the resulting solution so as to adjust the final volume thereof to 500 ml. The resulting solution was subject to sterile filtration with a 0.22 μm PVDF syringe filter to prepare a 4 w/v % eye drop solution.

Example 5

After phosphoric acid (0.0425 g), sodium hydrogen phosphate (4.43 g), and potassium dihydrogen phosphate (0.29 g) were dissolved in purified water (400 mL) under stirring at 50 rpm, sulglycotide (10 g) was dissolved therein. Hydroxypropyl methylcellulose (1 g) and sodium chloride (2.4 g) were dissolved in the resulting solution. Purified water was added to the resulting solution so as to adjust the final volume thereof to 500 ml. The resulting solution was subject to sterile filtration with a 0.22 μm PVDF syringe filter to prepare a 2 w/v % eye drop solution.

Examples 6 to 15

The eye drop solutions were prepared according to the components and amounts shown in Table 1. After the buffering agent was dissolved in purified water (800 mL) under stirring at 50 rpm, sulglycotide was dissolved therein. The isotonic agent, the viscosity-adjusting agent (Examples 9 and 14), and the antioxidant (Examples 10 and 15) were dissolved in the resulting solution. After the pH of the resulting solution was adjusted to about pH 7 with the pH-adjusting agent, purified water was added to the resulting solution so as to adjust the final volume thereof to 1000 ml. The resulting solution was subject to sterile filtration with a 0.22 μm PVDF syringe filter to prepare eye drop solutions.

TABLE 1

| | | Example | | | | | | | | | |
|---|---|---|---|---|---|---|---|---|---|---|---|
| | Component | 6 | 7 | 8 | 9 | 10 | 11 | 12 | 13 | 14 | 15 |
| Active ingredient | Sulglycotide (g) | 0.1 | 1 | 5 | 25 | 70 | 100 | 200 | 300 | 40 | 20 |
| Buffering agent | Phosphoric acid (g) | 0.09 | | | 0.09 | 0.09 | 0.09 | | 0.09 | 0.09 | 0.09 |
| | Sodium hydrogen phosphate (g) | 8.86 | | | 8.86 | 8.86 | 8.86 | | 8.86 | 8.86 | 8.86 |
| | Boric acid(g) | | 0.2 | 0.2 | | | | 0.2 | | | |
| | Sodium borate (g) | | 9.9 | 9.9 | | | | 9.9 | | | |
| Isotonic agent | Sodium chloride(g) | 4.8 | 4.8 | | | 4 | 4 | 4 | 4 | | |
| | Sorbitol(g) | | | 10 | 10 | | | | | 10 | 10 |
| Viscosity-adjusting agent | Polyvinylpyrrolidone (g) | | | | | | | | | 5 | |
| | Hydroxypropyl methylcellulose (g) | | | | 5 | | | | | | |
| Anti-oxidant | Butylated hydroxytoluene (g) | | | | | 1 | | | | | 1 |
| pH-adjusting agent | Sodium hydroxide | q.s. | q.s. | q.s. | q.s. | q.s. | q.s. | q.s. | q.s. | q.s. | q.s. |
| | Hydrochloric acid | q.s. | q.s. | q.s. | q.s. | q.s. | q.s. | q.s. | q.s. | q.s. | q.s. |
| Solvent | Purified water (final volume, ml) | 1000 | 1000 | 1000 | 1000 | 1000 | 1000 | 1000 | 1000 | 1000 | 1000 |

EXPERIMENTAL EXAMPLE

1. Methods (1) Mouse Model of Dry Eye and Experimental Procedures

The NOD·B10·H2$^b$ mice were purchased from Jackson Laboratory (Bar Harbor, Me., USA). 12- to 16-week-old male NOD·B10·H2$^b$ mice underwent desiccation stress via exposure to an air draft from a fan at an ambient humidity of 30-40% for 18 hours per day for 10 days, and a subcutaneous 0.2 mL injection of 0.5 mg/0.2 mL scopolamine hydrobromide (Sigma-Aldrich, St. Louis, Mo.) into alternating hindquarters four times (8 AM, 11 AM, 2 PM and 5 PM) per day, so as to induce dry eyes. During these experiments, the animals' behavior and food and water intake were not restricted. After inducing dry eyes, the desiccation stress was removed by discontinuing the scopolamine injections and placing the mice in an environment with normal humidity and temperature.

The non-treated normal NOD·B10·H2$^b$ mice were assigned to the control group (Control, n=3). Each SOS 1 to SOS 5 group was divided into the dry eye-induced group and the eye drop-administered group, respectively, as in the following table 2. In the eye drop-administered group of each SOS 1 to SOS 5 group, the eye drop solutions of Examples 1 to 5 (5 μL/eye) were respectively instilled bilaterally four times (8 AM, 11 AM, 2 PM and 5 PM) per day for 10 days after the removal of the desiccation stress.

TABLE 2

| | Dry eye-induced group (DS 10 D, n = 3) | Eye drop-administered group (n = 3) |
|---|---|---|
| SOS 1 | Dry eye-induced mice | Mice instilled with the eye drop solution of Example 1 |
| SOS 2 | Dry eye-induced mice | Mice instilled with the eye drop solution of Example 2 |
| SOS 3 | Dry eye-induced mice | Mice instilled with the eye drop solution of Example 3 |
| SOS 4 | Dry eye-induced mice | Mice instilled with the eye drop |

TABLE 2-continued

|  | Dry eye-induced group (DS 10 D, n = 3) | Eye drop-administered group (n = 3) |
|---|---|---|
| SOS 5 | Dry eye-induced mice | solution of Example 4<br>Mice instilled with the eye drop solution of Example 5 |

(2) Measurement of Tear Production

Tear production was measured with phenol red-impregnated cotton threads, as previously described (Oh H N, Kim C E, Lee J H, Yang J W. Effects of Quercetin in a Mouse Model of Experimental Dry Eye. Cornea. 2015; 34:1130-6). The phenol red-impregnated cotton threads (Zone-quick, Oasis, Glendora, Calif.) were held with jeweler's forceps and placed in the lateral canthus for 20 seconds. The tear volumes were expressed as the millimeters of wet thread that had been turned red by tears as measured under a microscope (SZX7; Olympus Corp., Tokyo, Japan). The tear fluid uptake was measured in millimeters and compared to a standard curve that was prepared from cotton threads with known uptake volumes of a stock basic solution (1500 mL of 0.9% saline and 5 mL of 5 N NaOH) over 20 seconds and was within the range that would be expected for mouse tears (Villareal A L, Farley W, Pflugfelder S C. Effect of topical ophthalmic epinastine and olopatadine on tear volume in mice. Eye Contact Lens. 2006; 32:272-6; Chen Z, Li Z, Basti S, Farley W J, Pflugfelder S C. Altered morphology and function of the lacrimal functional unit in protein kinase C alpha knockout mice. Invest Ophthalmol Vis Sci. 2010; 51:5592-600). The tear production was measured in both eyes, and the average value of both eyes was analyzed.

(3) Evaluation of Corneal Smoothness

The reflected images of the white ring of a fiber optic ring illuminator of a stereoscopic zoom microscope were obtained immediately after euthanasia. The corneal smoothness was assessed by two blinded observers who graded the distortion of the white ring as a reflection off the corneal epithelium in the digital images as previously described (De Paiva C S, Corrales R M, Villarreal A L, Farley W, Li D Q, Stern M E, Pflugfelder S C. Apical corneal barrier disruption in experimental murine dry eye is abrogated by methylprednisolone and doxycycline. Invest Ophthalmol Vis Sci. 2006; 47:2847-56). The corneal smoothness was measured in both eyes, and the average value of both eyes was measured. The corneal irregularity severity scores were calculated using a five-point scale that was based on the number of distorted quarters in the reflected ring and were graded as follows: 0, no distortion; 1, distortion in one quarter; 2, distortion in two quarters; 3, distortion in three quarters; 4, distortion in all four quarters; and 5, distortion so severe that no section of the ring was recognized.

(4) Measurement of Corneal Fluorescein Staining

Corneal fluorescein staining was performed as described by Rashid et al (Rashid S, Jin Y, Ecoiffier T, Barabino S, Schaumberg D A, Dana M R. Topical omega-3 and omega-6 fatty acids for treatment of dry eye. Arch Ophthalmol. 2008; 126:219-25). Sodium fluorescein (1%), 1 µL, was applied to the cornea of mice under anesthesia. Three minutes later, eyes were flushed with PBS to remove excess fluorescein, and corneal staining was evaluated and photographed with a slit lamp biomicroscope (SL-D7; Topcon, Tokyo, Japan) using a cobalt blue light. Punctate staining was recorded using a standardized National Eye Institute grading system of 0 to 3 for each of the five areas of the cornea (Lemp M A. Report of the National Eye Institute/Industry Workshop on Clinical Trials in Dry Eyes. Clao J. 1995; 21:221-32).

(5) Histology

The eyes and adnexa of each group were surgically excised, fixed in 10% formalin, and embedded in paraffin. Six-micrometer sections were stained with H&E (hematoxylinand eosin) and PAS (periodic-Schiff). In case of the conjunctiva, the number of detached epithelial cells in an area of 0.1 mm$^2$ thereof was calculated by the H&E staining. In case of the conjunctival tissues, the number of goblet cells in the conjunctival inferior fornix was evaluated in an area of 0.1 mm$^2$ thereof by the PAS staining. The number of detached corneal epithelial cells and the number of conjunctival goblet cells were measured by averaging the data from three non-consecutive cross-section slides for each mouse and 3 or 4 mice per group. The sections from each group were examined and imaged using a Virtual Microscope (NanoZoomer 2.0 RS, Hamamatsu, Japan).

(6) Immunohistochemistry

The eyes and adnexa were surgically excised, embedded in paraffin, and flash frozen in liquid nitrogen. Six-micrometer sections were cut with a cryostat. The sections were fixed with pre-cooled acetone for 5 minutes, and the primary antibodies for TNF-α (Abcam Inc., Cambridge, Mass.), MMP-2 (Abcam Inc., Cambridge, Mass.), MMP-9 (Lifespan Biosciences Inc., Seattle, Wash.), ICAM-1 (Bioss Inc., Woburn, Mass.), and VCAM-1 (Bioss Inc., Woburn, Mass.) were applied and incubated for 1 hour at room temperature. After washing, the sections were incubated with secondary antibody (DAKO Corp, Glostrup, Denmark) for 30 minutes. Immunoreactions were visualized to with diaminobenzidine chromogen, and the sections were counterstained with Mayer's hematoxylin (Sigma) for 30 seconds at room temperature. Images of the sections were photographed with a Virtual Microscope (NanoZoomer 2.0 RS, Hamamatsu, Japan).

(7) Statistical Analyses

The data were analyzed with SPSS version 18.0 (SPSS, Chicago, Ill., USA) and expressed as mean±SD. The differences between groups were analyzed using 2-way analyses of variance (analyses of variance with Tukey's test), and statistical significance was defined as $P<0.05$.

2. Results (1) Effects of the Sulglycotide-Containing Eye Drop Solutions on Alterations in Tear Production As shown in FIG. 1, the SOS 1 group exhibited a 6.7-fold increase after 10 days (0.165±0.027 µL) compared to the DS 10D group (0.025±0.008 µL) ($P<0.05$); the SOS 2 group exhibited a 7.6-fold increase after 10 days (0.157±0.027 µL) compared to the DS 10D group (0.021±0.009 µL) ($P<0.05$); the SOS 3 group exhibited a 8.5-fold increase after 10 days (0.176±0.030 µL) compared to the DS 10D group (0.021±0.009 µL) ($P<0.05$); the SOS 4 group exhibited a 14.6-fold increase after 10 days (0.246±0.022 µL) compared to the DS 10D group (0.017±0.008 µL) ($P<0.05$); and the SOS 5 group exhibited a 15.5-fold increase after 10 days (0.262±0.018 µL) compared to the DS 10D group (0.017±0.008 µL) ($P<0.05$). Instillation of the sulglycotide-containing eye drop solutions after the removal of the desiccation stress resulted in tear volumes that gradually improved, compared to the DS 10D group. In particular, tear volumes was observed that an increase to the control levels in the SOS 4 and 5 groups.

Figure 2:
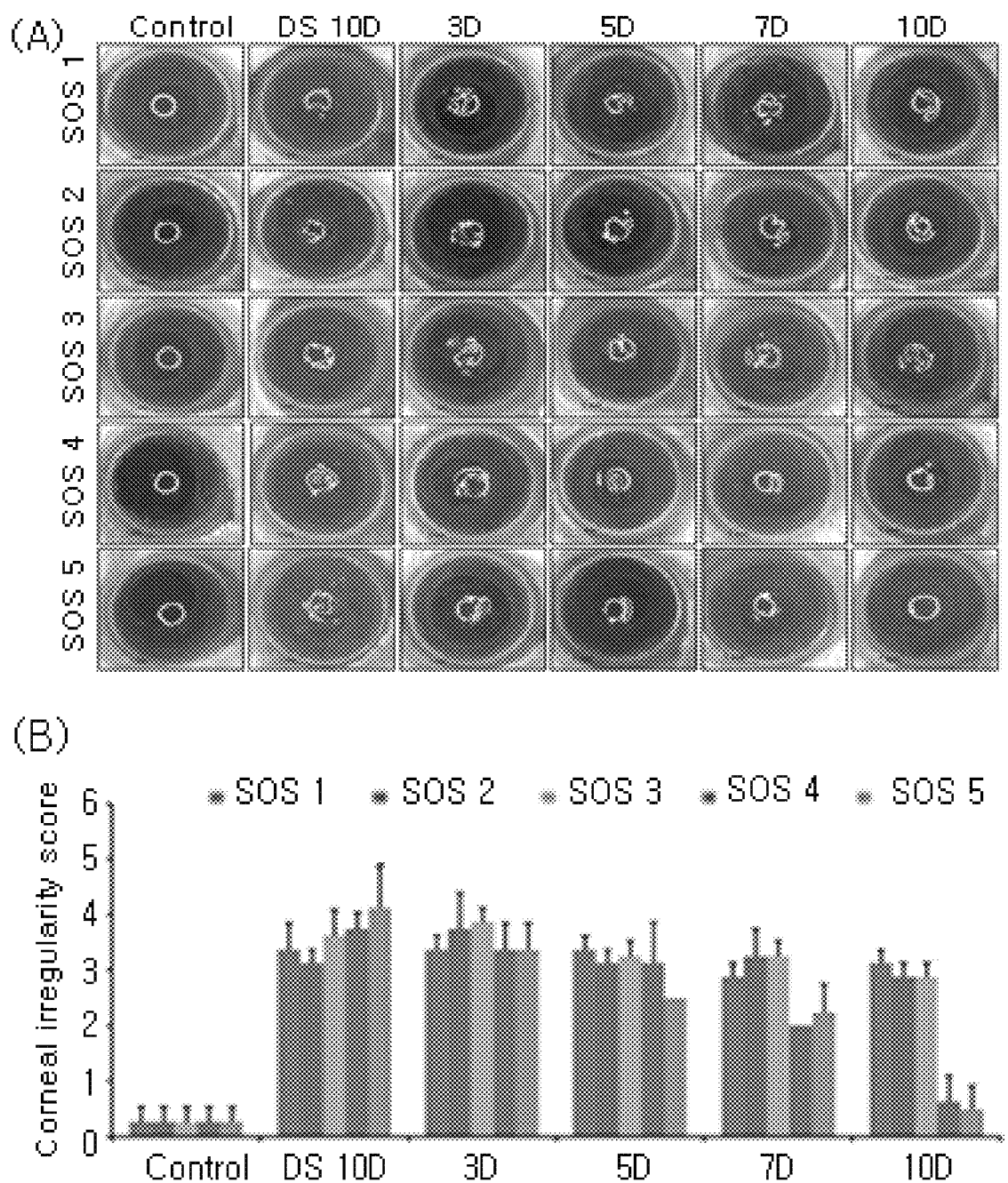
FIG. 2 shows the effects of the sulglycotide-containing eye drop solutions on corneal surface irregularities in the dry eye animal models (DED).

(2) Effects of the Sulglycotide-Containing Eye Drop Solutions on Corneal Surface Irregularities As shown in FIG. 2, the corneal irregularity score of the DS 10D group (3.375±0.479 score) exhibited a 13.5-fold increase compared to the control (0.250±0.289 score), and the decrease observed in the SOS 1 group was 7.4% at 10 days (3.125±0.250 score) (P<0.05). In addition, the corneal surface irregularities observed in the SOS 2 and SOS 3 groups decreased by 8% and 20.7% at 10 days (2.875±0.250 and 2.875±0.250 score), respectively, compared to the DS 10D group (P<0.05). The irregularities in the SOS 4 and SOS 5 groups decreased by 83.3% and 87.9% at 10 days (0.625±0.479 and 0.500±0.408 score), respectively, compared to the DS 10D group (P<0.05). Especially, the distortion of the white ring in the SOS 4 and SOS 5 groups improved to the control level observed by days 10.

Figure 3:
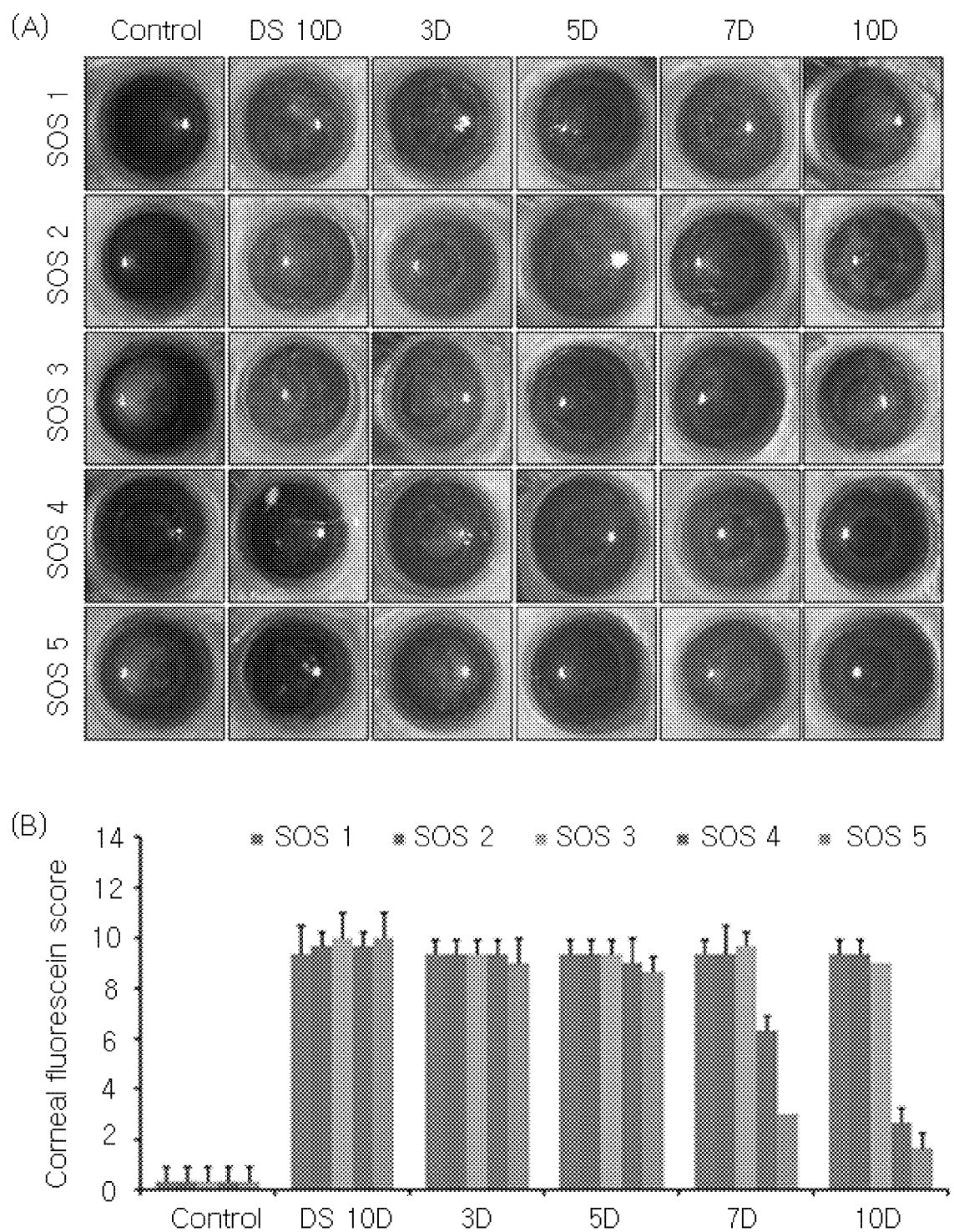
FIG. 3 shows the effects of the sulglycotide-containing eye drop solutions on corneal fluorescein staining in the dry eye animal models (DED).

(3) Effects of the Sulglycotide-Containing Eye Drop Solutions on Corneal Fluorescein Staining As shown in FIG. 3, control cornea did not show any uptake of the fluorescent dye, indicating an intact epithelial barrier. However, DS 10D cornea showed a patchy staining pattern, exhibiting a damaged corneal epithelial barrier. The corneal fluorescein score of the DS 10D group (9.333±1.155 score) exhibited a 28-fold increase compared to the control (0.333±0.577 score), and did not decrease in the SOS 1 group at 10 days (9.333±0.577 score) (P<0.05). However, the corneal fluorescein score observed in the SOS 2 and SOS 3 groups decreased by 3.4% and 10% at 10 days (9.333±0.577 and 9.0±0 score), respectively, compared to the DS 10D group (P<0.05). And also, the corneal fluorescein score observed in the SOS 4 and SOS 5 groups decreased by 72.4% and 83.3% at 10 days (2.667±0.577 and 1.667±0.577 score), respectively, compared to the DS 10D group (P<0.05). Especially, damage of corneal epithelial barrier in the SOS 4 and SOS 5 groups at 10 days improved to the control level.

Figure 4:
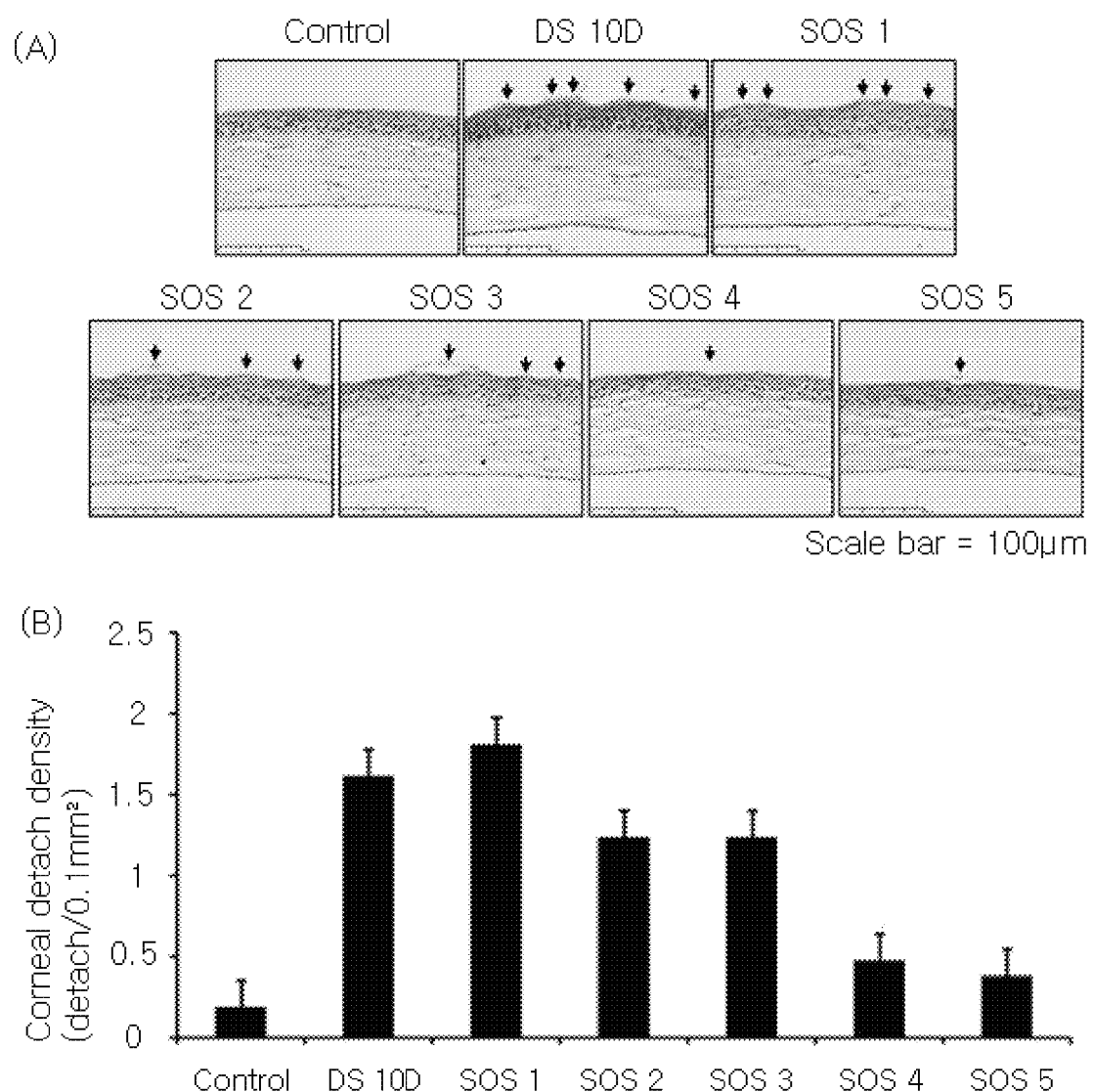
FIG. 4 shows the effects of the sulglycotide-containing eye drop solutions on detachment of corneal epithelial cells in the dry eye animal models (DED).

(4) Effects of the Sulglycotide-Containing Eye Drop Solutions on the Detachment of Corneal Epithelial Cells As shown in FIG. 4, the number of detached corneal epithelial cells was increased by 8.5-fold in the DS 10D group (1.619±0.165 cells/0.1 mm$^2$) compared to the control (0.190±0.165 cells/0.1 mm$^2$) (P<0.05). The number of detached corneal epithelial cells was increased by 1.1-fold in the SOS 1 group (1.810±0.165 cells/0.1 mm$^2$), compared to the DS 10D group (P<0.05). In contrast, the number of detached corneal epithelial cells observed in the SOS 2 and SOS 3 groups (1.238±0.165 and 1.238±0.165 cells/0.1 mm$^2$) was decreased by 23.5% and 23.5%, respectively, compared to the DS 10D group (P<0.05). In addition, the numbers of the detachment of corneal epithelial cells decreased by 70.6% and 76.5% in the SOS 4 and SOS 5 groups (0.476±0.165 and 0.381±0.165 cells/0.1 mm$^2$), respectively, compared to the DS 10D group (P<0.05).

Figure 5:
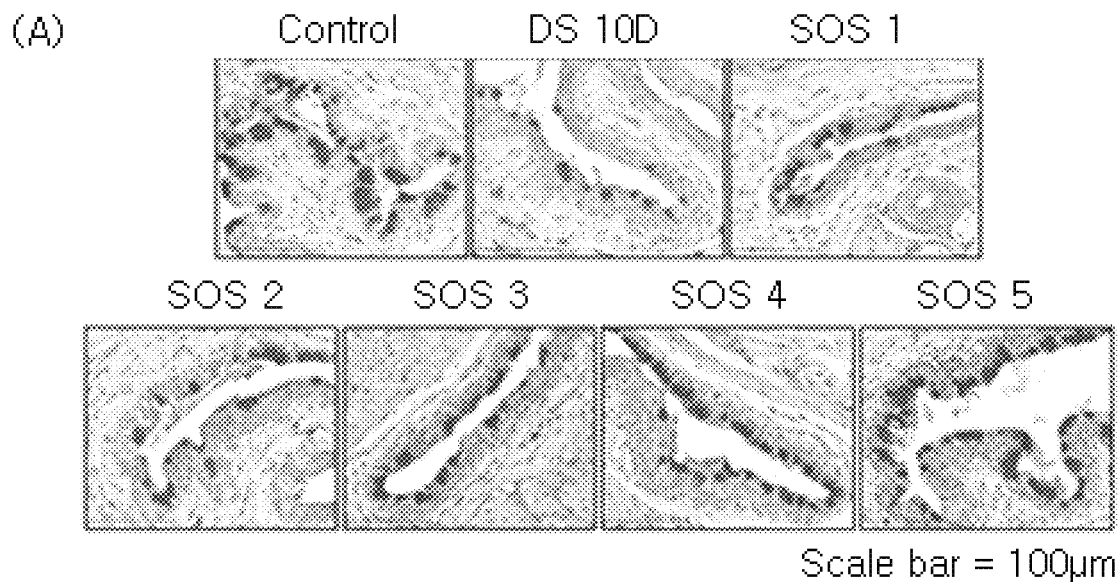
FIG. 5 shows the effects of the sulglycotide-containing eye drop solutions on conjunctival goblet cell densities in the dry eye animal models (DED).
Figure 5:
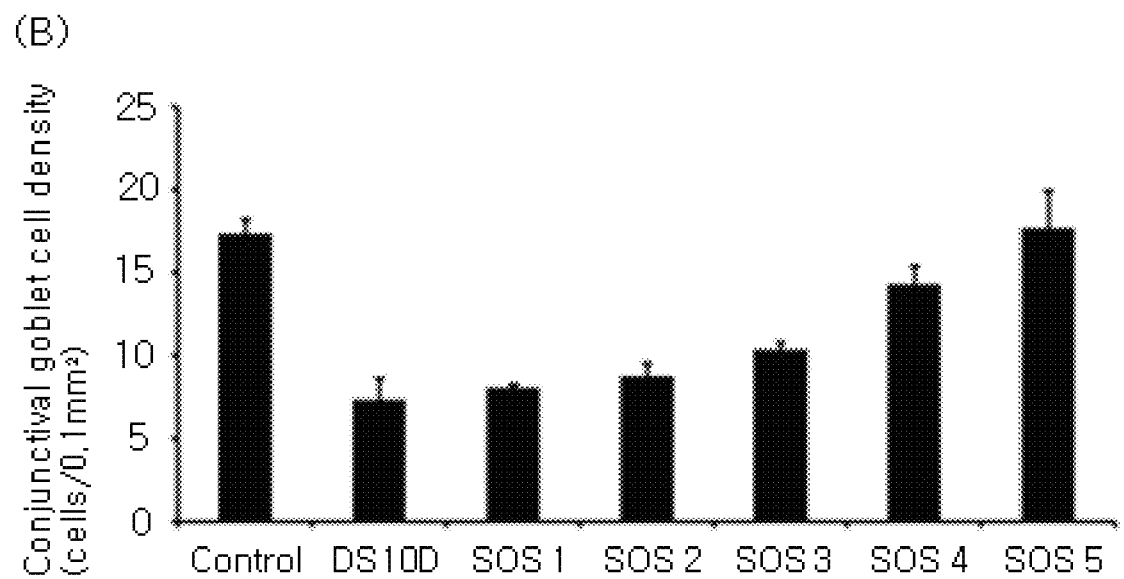

(5) Effects of the Sulglycotide-Containing Eye Drop Solutions on the Conjunctival Goblet Cells As shown in FIG. 5, the number of conjunctival goblet cells were decreased by 57.7% in the DS 10D group (7.333±1.288 cells/0.1 mm$^2$) compared to the control (17.333±0.873 cells/0.1 mm$^2$), but increased by 1.1-fold in the SOS 1 group (8.095±0.165 cells/0.1 mm$^2$) compared to the DS 10D group (P<0.05). The number of conjunctival goblet cells were increased by 1.2-fold and 1.4-fold in the SOS 2 and SOS 3 groups (8.762±0.825 and 10.381±0.436 cells/0.1 mm$^2$), respectively, compared to the DS 10D group (P<0.05). In addition, the SOS 4 and SOS 5 groups (14.286±1.143 and 17.714±2.268 cells/0.1 mm$^2$) exhibited the increases by 1.9-fold and 2.4-fold, respectively, compared to the DS 10D group (P<0.05).

Figure 6:
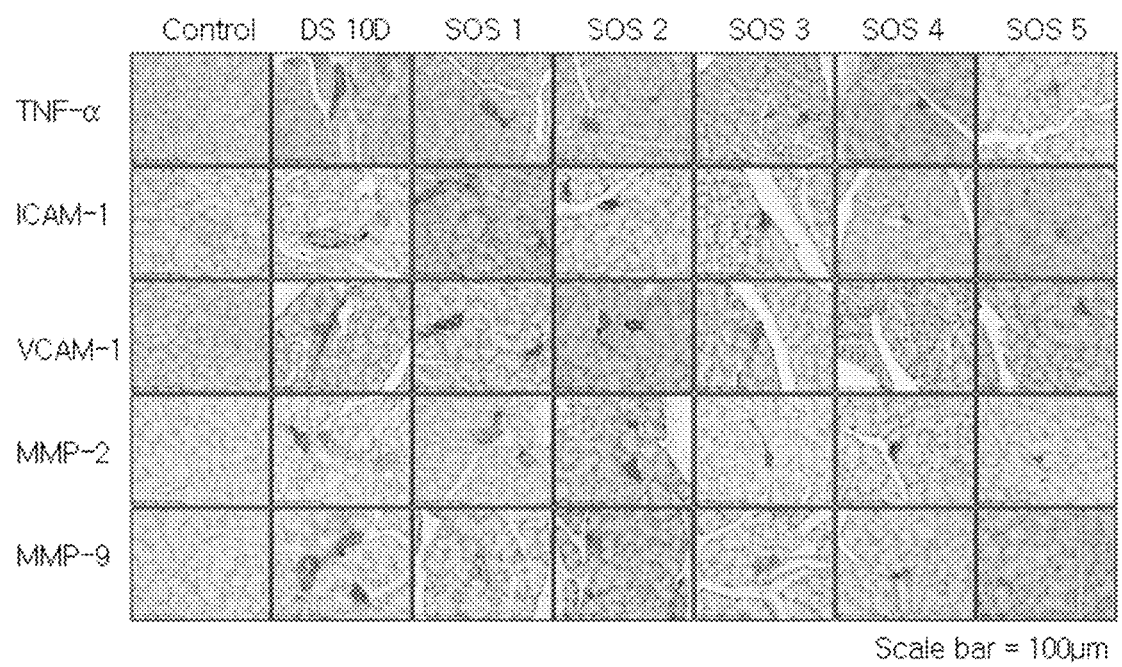
FIG. 6 shows the effects of the sulglycotide-containing eye drop solutions on inflammation in the dry eye animal models (DED).

(6) Anti-Inflammatory Effects of the Sulglycotide-Containing Eye Drop Solutions in the Dry Eye Mouse Model As shown in FIG. 6, sections of the lacrimal gland were immunostained for TNF-α, MMP-2, MMP-9, ICAM-1, and VCAM-1. The inflammatory marker TNF-α was significantly overexpressed in the lacrimal gland after the removal of desiccation stress. However, TNF-α expression was reduced in the SOS 4 and SOS 5 groups. Additionally, immunostaining for MMP-2 and MMP-9 also produced intense staining in the lacrimal gland, but this staining was significantly reduced in the SOS 4 and SOS 5 groups. Staining for ICAM-1 and VCAM-1 was highly restricted to the lacrimal gland in the DS 10D group. These positive markers of lacrimal gland were suppressed in the SOS 4 and SOS 5 groups compared to the DS 10D group.

The invention claimed is:

1. A method of treating a dry eye syndrome in a subject in need thereof, comprising administering to the subject a pharmaceutical composition comprising an effective amount of sulglycotide or a pharmaceutically acceptable salt thereof.

2. The method of claim 1, wherein sulglycotide or the pharmaceutically acceptable salt thereof is present in a concentration of 0.01 w/v % to 30 w/v %.

3. The method of claim 1, wherein the pharmaceutical composition is an eye drop formulation.

4. The method of claim 3, wherein the eye drop formulation is in the form of an aqueous solution or an aqueous suspension.

5. The method of claim 3, wherein the eye drop formulation further comprises one or more pharmaceutically acceptable carrier(s) or excipient(s) selected from the group consisting of a buffering agent, a viscosity-adjusting agent, an isotonic agent, an antioxidant, a chelating agent and a pH-adjusting agent, in an aqueous medium.

6. The method of claim 5, wherein the viscosity-adjusting agent is one or more selected from the group consisting of polyvinyl alcohol, polyvinylpyrrolidone, methyl cellulose, hydroxypropyl methylcellulose, hydroxyethyl cellulose, carboxymethyl cellulose, and hydroxypropyl cellulose.

7. The method of claim 6, wherein the viscosity-adjusting agent is polyvinylpyrrolidone or hydroxypropyl methylcellulose.

* * * * *